United States Patent
Keynan

(10) Patent No.: US 6,755,862 B2
(45) Date of Patent: Jun. 29, 2004

(54) INTRAMEDULLARY SUPPORT STRUT

(75) Inventor: Ory Keynan, Givataim (IL)

(73) Assignee: Orthoscope Ltd., Herzlyia (IL)

(*) Notice: Subject to any disclaimer, the term of this patent is extended or adjusted under 35 U.S.C. 154(b) by 0 days.

(21) Appl. No.: 10/188,125

(22) Filed: Jul. 2, 2002

(65) Prior Publication Data

US 2003/0109932 A1 Jun. 12, 2003

Related U.S. Application Data

(63) Continuation of application No. PCT/IL01/00002, filed on Jan. 1, 2001.

(30) Foreign Application Priority Data

Jan. 3, 2000 (IL) ................................................. 133873
Jan. 3, 2000 (IL) ................................................. 133874

(51) Int. Cl.[7] ................................................. A61F 2/28
(52) U.S. Cl. ........................ 623/16.11; 606/63; 606/170
(58) Field of Search ............................... 606/63, 64, 68, 606/89, 80, 94, 104, 105, 108, 170, 180, 192, 198; 623/16.11, 17.12, 19.14, 20.25, 20.35, 20.36, 22.4, 22.41–22.46, 23.23, 23.26, 23.27, 23.32, 23.33, 23.45, 23.47; 411/82.1, 19, 32

(56) References Cited

U.S. PATENT DOCUMENTS

| | | | |
|---|---|---|---|
| 2,672,861 A | | 3/1954 | Jonas et al. |
| 3,441,017 A | * | 4/1969 | Kaessmann .................. 606/64 |
| 3,680,553 A | * | 8/1972 | Seppo .......................... 606/71 |
| 4,190,044 A | | 2/1980 | Wood |
| 4,379,451 A | | 4/1983 | Getscher |
| 4,714,478 A | | 12/1987 | Fischer |
| 4,795,473 A | | 1/1989 | Grimes |
| 4,936,856 A | | 6/1990 | Keller |
| 5,071,435 A | * | 12/1991 | Fuchs et al. .................. 623/16 |
| 5,269,785 A | * | 12/1993 | Bonutti ........................ 606/80 |
| 5,314,479 A | * | 5/1994 | Rockwood, Jr. et al. ...... 623/19 |
| 5,415,660 A | * | 5/1995 | Campbell et al. ............. 606/62 |
| 5,626,579 A | * | 5/1997 | Muschler et al. ............. 606/60 |
| 5,645,545 A | * | 7/1997 | Bryant ........................ 606/62 |
| 5,997,582 A | | 12/1999 | Weiss |
| 6,183,516 B1 | * | 2/2001 | Burkinshaw et al. .... 623/16.11 |

FOREIGN PATENT DOCUMENTS

| | | |
|---|---|---|
| DK | 44 38 620 | 11/1995 |
| DK | 197 52 674 | 6/1999 |
| EP | 099 167 | 1/1984 |
| EP | 382 395 | 8/1990 |
| EP | 0913129 | 5/1999 |
| SU | 749 392 | 7/1980 |
| WO | WO 89 11837 | 12/1989 |
| WO | WO 95/22292 | 8/1995 |
| WO | WO 98 34567 | 8/1998 |
| WO | WO 00 090 38 | 2/2000 |
| WO | WO 00 09044 | 2/2000 |

* cited by examiner

Primary Examiner—Eduardo C. Robert
Assistant Examiner—David Comstock
(74) Attorney, Agent, or Firm—Frommer Lawrence & Haug, LLP; William S. Frommer; Darren M. Simon

(57) ABSTRACT

An intramedullary support strut for a long bone for a range of different applications including anchoring and fixation. The strut is in the form of nested telescopic members. In the retracted configuration, the strut is compact and may be inserted into position aligned with a shaft made in the medullary canal via a portal made in the lateral cortex of the bone. The strut may then be telescopically extended into the medullary canal to provide the required support.

42 Claims, 12 Drawing Sheets

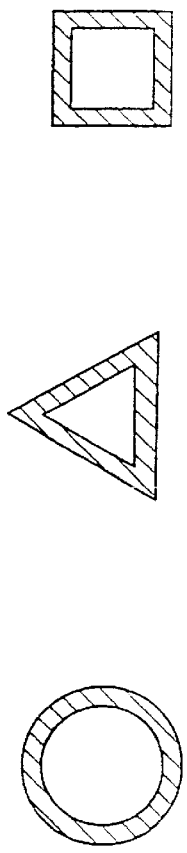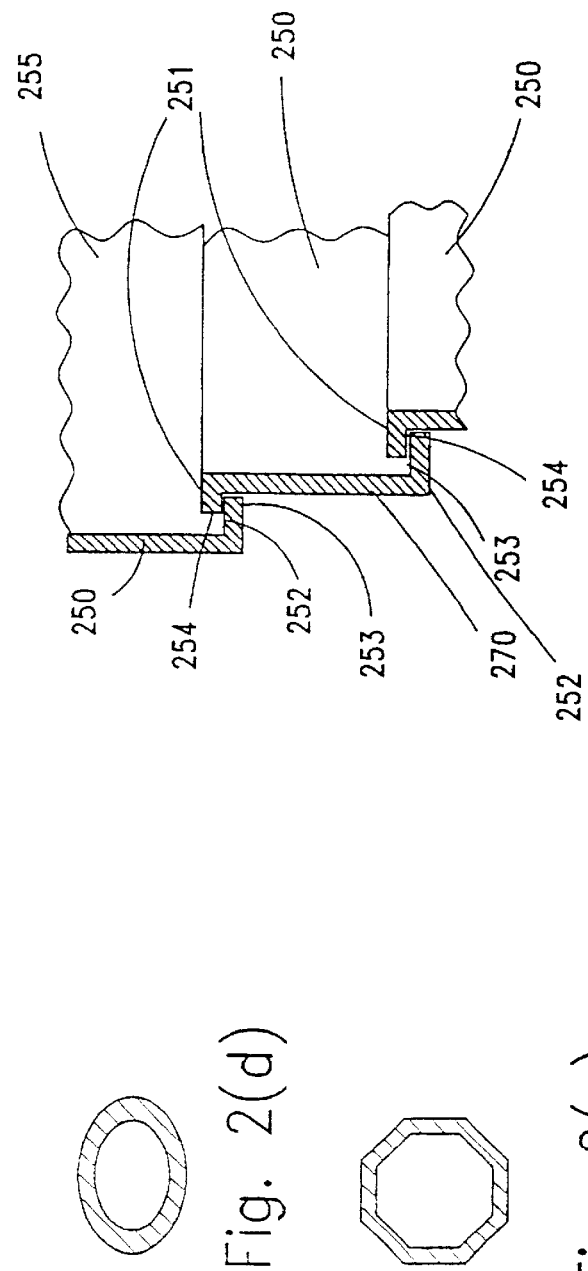

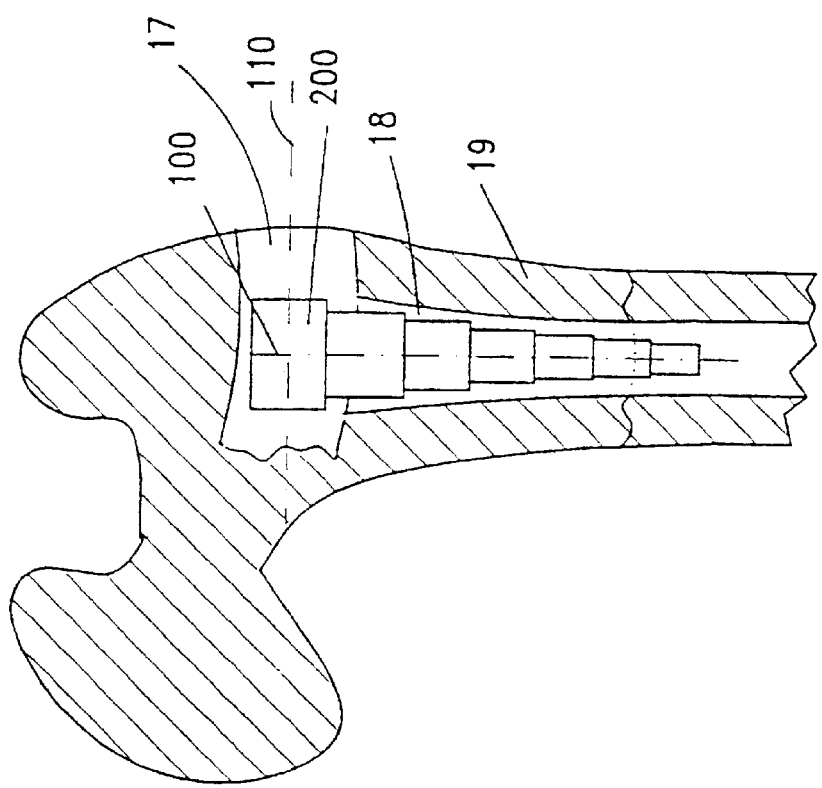
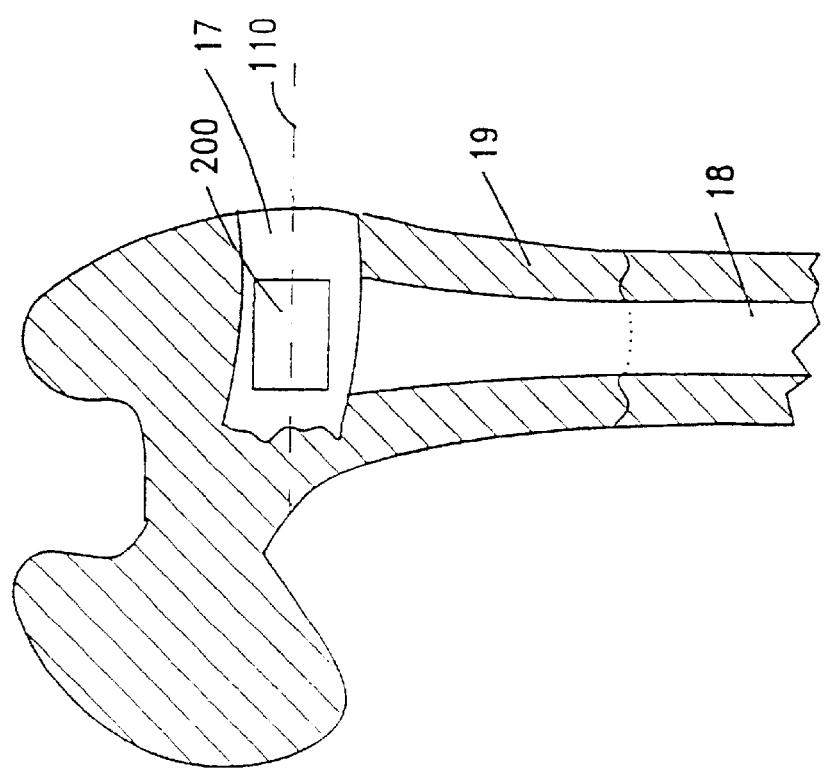

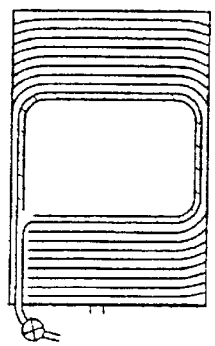
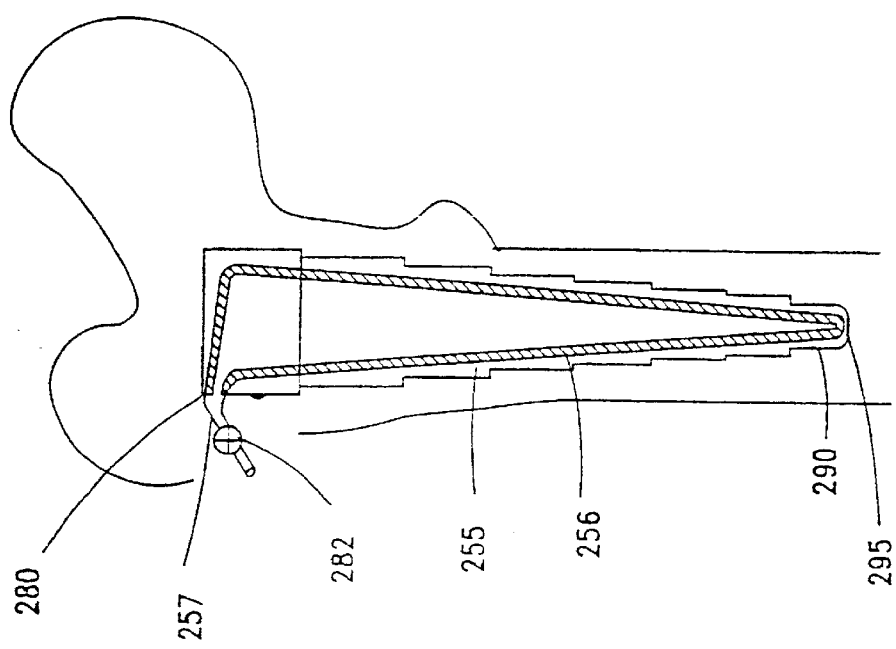
Fig. 5(a)
Fig. 5(b)

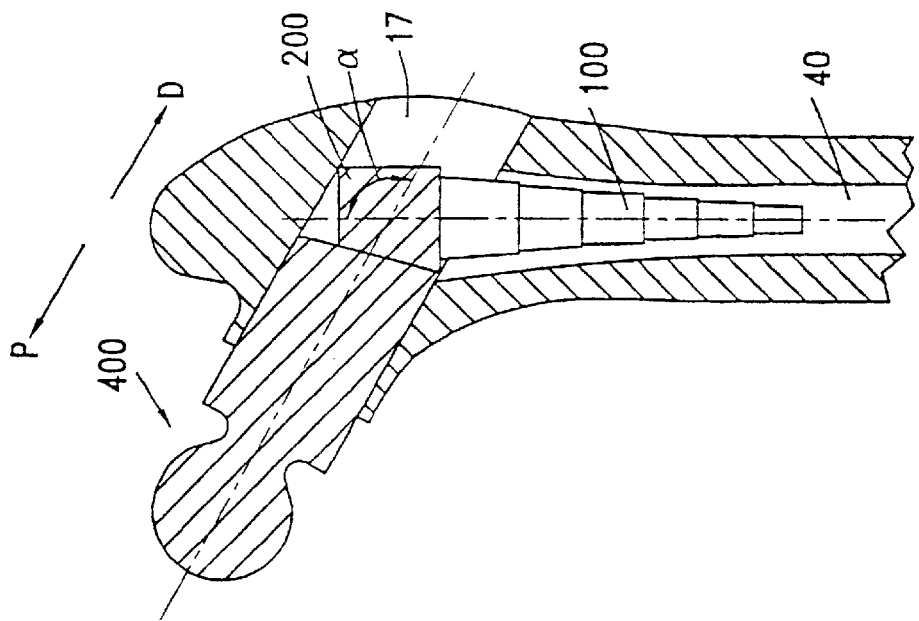
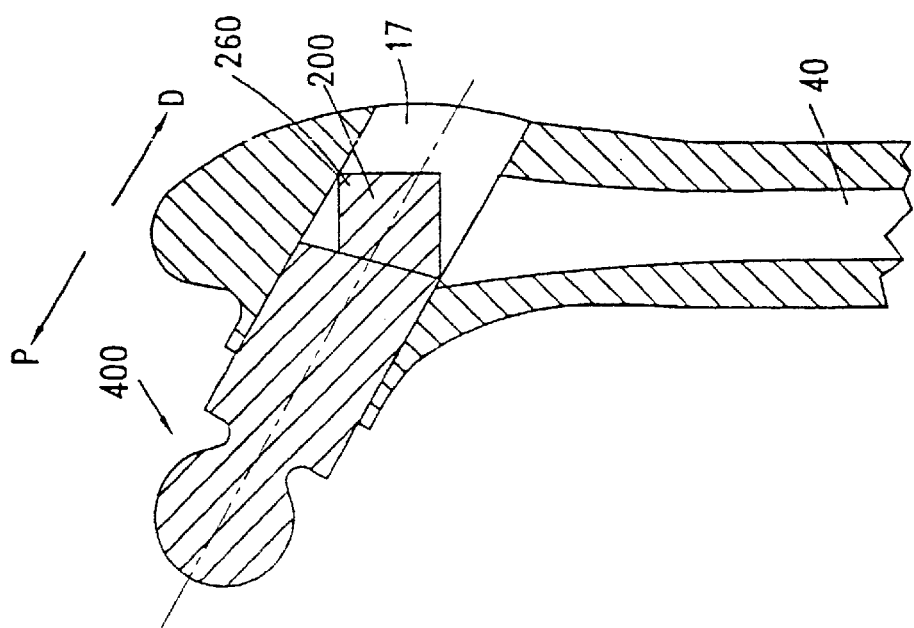

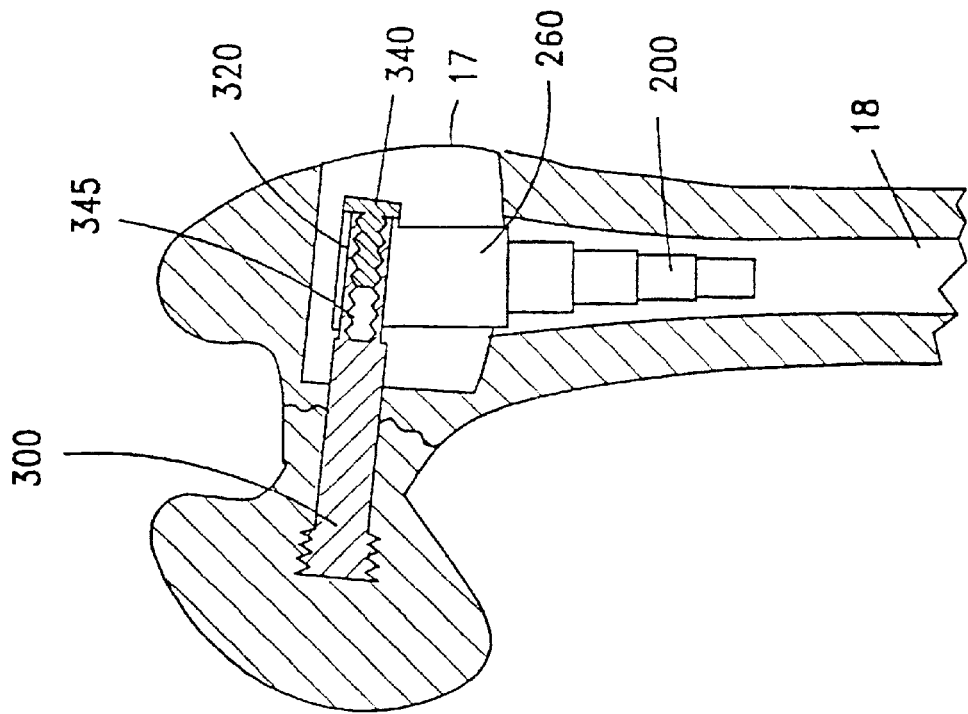
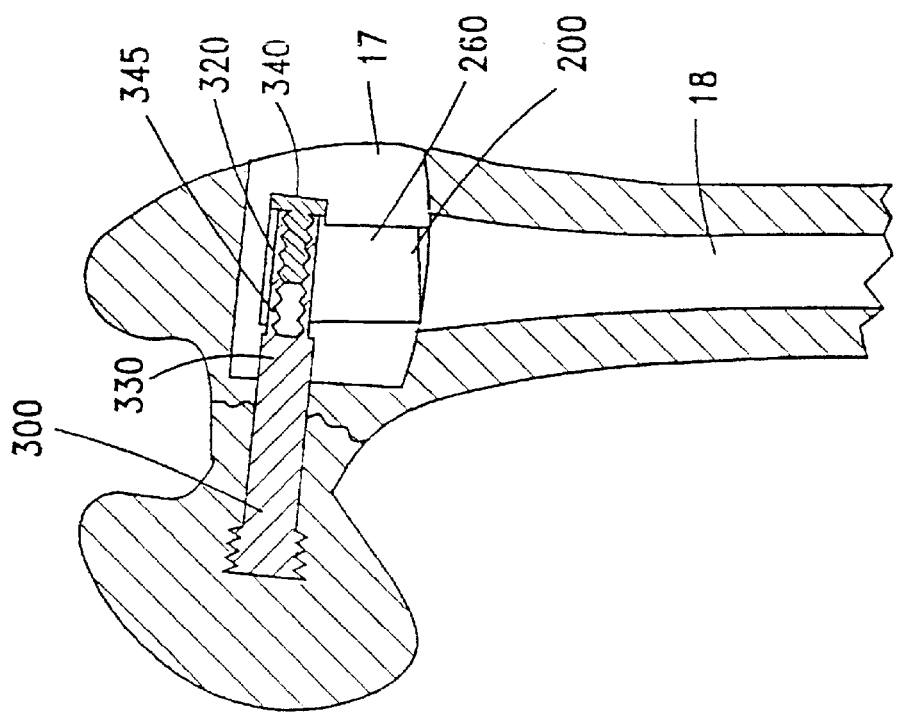
Fig. 13(a)
Fig. 13(b)

INTRAMEDULLARY SUPPORT STRUT

This is a continuation of copending international application PCT/IL01/00002 having an international filing date of Jan. 1, 2001.

TECHNICAL FIELD

The present invention relates to an intramedullary support strut for long bones, in particular such a support strut that is expandable from a compact configuration to an extended configuration such as to enable the strut to be inserted into the medullary canal of long bones via a relatively small lateral portal made on the side of the bone.

BACKGROUND

Diaphyseal fractures of long bones such as the humerus, femur and tibia usually require surgical fixation. Current solutions for such fractures include external fixation and internal fixation. Internal fixation can be divided further into extramnedullary fixation (plate and screws) and the more popular intramedullary fixation. Intrarnedulary fixation consists of nails, which can be classified into flexible, rigid, interlocking and non-interlocking. Interlocking nails are fixed at their ends by screws perpendicular to the axis of the nail, through separate incisions and bony windows or portals. The current popular solutions for isolated subtrochanteric fractures or combined intertrochanteric/subcapital and subtrochanteric fractures consist of compression screw/nail-plate systems with long side plate or intramedullary interlocking nail combined with screw extension into the femoral neck and head. The current solutions for two and three-part proximal humeral fractures (mainly subcapital fractures) include fixation with wires, nails, plates, screws, intramedullary rods, and combinations of the above.

The above solutions have several limitations. For example, in diaphyseal fractures, the plating requires a large skin incision, extensive soft tissue exposure, and stripping of the bone. Intramedullary nailing requires an extensive surgical approach and exposure at the entry site with some bones, and poses risk to important neurovascular structures in others. In isolated proximal femoral fractures and combined intertrochanteric/subtrochanteric femoral fractures, both the screw/plate system and intramedullary nail/screw system require extensive surgical approaches and multiple apertures in the bone. Complications of nail/screw-plate system when applied to the combined fractures are more common than when applied to isolated inter/subtrochanteric fractures, and include loosening of plate screws, failure of plate or plate screw, and higher rates of infection. Regarding proximal humeral fractures, all of the above mentioned techniques fail to demonstrate a consistently stable fixation and a good solution for these fractures is currently lacking.

As it is well established that intramedullary anchoring of fracture fixation devices (screw/nail) in the proximal femur is biomechanically superior to side-plate anchoring of these devices, intramedullary anchoring has become the method of choice for fixation of the more problematic subtrochanteric and combined inter/subtrochantenc fractures. For isolated intertrochantenc fractures, the side plate anchoring system is still the method of choice. This is because of the extensive surgical approach and multiple bony entry points involved with the currently available combination screw-intramedullary nail systems is deemed unjustifiable. However, the combination of a solution that provides both the biomechanical stability of intramedullarv fixation and a minimally invasive surgical approach, would appear to be particularly advantageous.

All currently used techniques for reducing and fixating subcapital humeral fractures have ultimately proven to be unsatisfactory in one way or another. Therefore, any solution to these problematic fractures that would consistently demonstrate satisfactory results would constitute an improvement.

WO 95 22292 discloses a tissue lengthening device for lengthening a bone, and is not concerned with providing mechanical support for the bone. In this reference, both the distal and proximal portions of the device are fully anchored in the bone before any relative movement commences between the two portions of the device. Thus, this is the "retracted" configuration of this device, which has to be inserted into the long bone via a superior portal made in the bone. The device cannot be introduced into the medullary canal via a transverse portal made in the bone, since such a portal would have to comprise the length of the device, i.e., approximately the longitudinal length of the bone, which would be needlessly destructive to the bone and surrounding tissues. Further, the device does not extend into the bone, but remains where it is relative to the medullary canal, and instead lengthens the bone slowly, in registry with the extension of the device itself.

U.S. Pat. No. 4,190,044 is directed to an intermedullary pin for the repair of a bone. The pin has two sections, an inner section of which is retracted into the other outer section. The pin is inserted into one of the two broken bone fragments via a medullary opening at the break, and then the two halves of the bones are aligned together. Thereafter, by means of a wire, the inner section of the pin is extended into the medullary canal of the second bone fragment, again via the break. Thus, the pin, in its "retracted" configuration, must be long enough to be well-anchored into the bone fragment, and moreover it is inserted therein longitudinally via the break in the fragment, rather than through a lateral portal, since the break in the bone already provides a portal for the pin.

U.S. Pat. No. 4,936,856 deals with an acetabular prosthesis to be supported in a cavity in the hip bone. The prosthesis comprises a socket member adapted for being anchored to the bone, and at least one elongated support adapted to be coupled with the socket member and configured to extend outwardly a variable length from the outer surface of the socket into the cavity. In one embodiment, the elongated support is in the form of a telescopically constructed support, wherein smallest diameter sleeve is extended outwardly from the socket until it reaches the bone in the cavity. The "telescopic constructed support" is but one manner proposed in this reference for providing a longitudinal support that extends from the socket to the bone within the cavity, and this "telescopic constructed support" is in any case provided on the socket via a longitudinal bore therein. The criterion defining the "retracted" configuration of the "telescopic constructed support" is that the longitudinal length of each element should not exceed that of the bore. There is no disclosure or suggestion of a support strut at all, less so with the characterizing feature of the present invention.

It is an aim of the present invention to provide a fixation device for accommodation in the medullary canal that overcomes the limitations of prior art devices.

It is another aim of the present invention to provide an intra-medullary support strut for long bones that has a variety of applications.

It is another aim of the present invention to provide a stem for a femoral head prosthesis or a humeral head prosthesis requiring a minimally invasive surgical approach for its implantation relative to currently used extensive methods of surgery.

It is another aim of the present invention to provide a stem for a femoral or humeral head prosthesis having a rigidity closer to that of bone thus reducing stress shielding encountered in currently available prostheses.

It is another aim of the present invention to provide a stem/anchor for screw/nail fixation devices of isolated and combined proximal femoral fractures, offering a more stable biomechanical fixation than side plate fixation of these devices.

It is another aim of the present invention to provide a stem/anchor for screw/nail fixation devices of isolated and combined proximal femoral fractures such that permit a minimal surgical approach.

It is another aim of the present invention to provide a fixation device for diaphyseal fractures in long bones requiring a less extensive surgical approach.

It is another aim of the present invention to provide a fixation device for proximal humeral fractures offering a stable fixation where no one universally accepted and consistently satisfactory solution exists.

SUMMARY OF INVENTION

The present invention relates to an intrarmedullary support strut for long bones comprising at least two telescopic members adapted for longitudinal displacement relative to each other from a retracted configuration of said strut having a first longitudinal length to an extended configuration of said strut having a second longitudinal length, wherein said strut is adapted in said extended configuration for accommodation in a longitudinal cavity formed in the medullary canal of said long bone and for providing therein a mechanical support structure for said long bone, and wherein said strut comprises in said retracted configuration a transverse profile adapted for enabling said strut to be inserted into said long bone via a suitable lateral portal formed through the lateral cortex of the long bone, such as to enable said strut to be aligned with and extended into said cavity.

Preferably, a most proximally disposed said telescopic member constitutes a base member adapted for remaining within said portal when said strut is in extended configuration. Optionally, said strut comprises a cap portion at the distal end of the innermost said telescopic member.

The ratio of the diameter of said strut to said first length is typically between about 0.5 and about 2.0, and preferably about 1.25, and the ratio of said second length to said first length is typically between about 3 and about 10, and preferably about 8. Typically, said strut comprises between 3 and 10, and preferably 8 said telescopic members.

Optionally, said telescopic members are adapted for sliding longitudinal displacement relative to each other from said retracted to said extended configuration. Alternatively, said telescopic members are adapted for longitudinal displacement relative to each other from said retracted configuration to said extended configuration by each said telescopic member having at least a portion of the inside surfaces thereof screw-threaded and at least a portion of their outside surfaces complimentary threaded to engage with the inside surface of the externally-adjacent telescopic member.

Optionally, each said telescopic member comprises a substantially circular, elliptical, triangular, rectangular or polygonal longitudinal cross-sectional profile. The lateral portal may be disposed at an angle between about 90° and about 150° to said longitudinal cavity.

Optionally, said intramedullary support strut further comprises actuating means for extending said strut from said retracted configuration to said extended configuration. The actuating means may comprise a liquid injected under pressure into said strut via a suitable openimg therein, or alternatively an inflatable bag in said strut and in communication with said opening for receiving said liquid and for preventing leakage of liquid therefrom, or alternatively a feeding wire arrangement comprising a wire having a distal end attached to the distal end of said innermost telescopic member, and a wire feeder for feeding said wire distally with respect to said base member. Such a feeding wire may be disposed external to said strut, or alternatively, the feeding wire is disposed internally in said strut, wherein said wire feeder comprises a spool for feeding said wire to said strut, said spool being operatively connected to a motor means.

Alternatively, the actuating means may comprise a suitable reamer having a suitable reamer head at one end thereof rotatably mounted, preferably permanently, with respect to an innermost telescopic member, wherein rotation of said reamer head and advancement thereof in a distal direction by suitable rotation means automatically opens the said strut. Preferably, said rotation means comprises a suitable power tool. Optionally, the reamer comprises a flexible reamer driveshaft removably connected to the said reamer head at one thereof, and to said power tool at the other end thereof. The reaming diameter of said reamer head may be at least equal to or greater than the diameter of said base member.

Alternatively, wherein said actuating means comprises a suitable reamer having a suitable reamer head at one end thereof releasably rotatably engageable with respect to an innermost telescopic member, wherein rotation of said reamer head and advancement thereof in a distal direction by suitable rotation means automatically opens the said strut. The reaming diameter of said reamer head is typically smaller than the diameter of said innermost telescopic member.

Said support strut optionally further comprises locking means for maintaining said strut in said extended configuration. The locking means may comprise suitable stops between adjacent said telescopic members adapted to prevent relative movement therebetween when said strut is in said extended configuration. Alternatively, the locking means may comprise an inflatable bag having an opening for receiving a suitable liquid, said bag adapted for maintaining said liquid at a suitable pressure. Altematively, the locking means comprises at least one semi-rigid bar insertable within said strut when said strut is in said extended configuration. Alternatively, the locking means comprises a screw or nail for locking the said innermost telescopic member with respect to said long bone, when said strut is in said extended configuration. Alternatively, the locking means comprises suitable bone cement provided between said strut and said cavity when said strut is in said extended configuration. Alternatively, the locking means comprises a suitable flowable polymer injected into said strut when said strut is in said extended configuration, said flowable polymer being adapted for setting and hardening in situ. Such a flowable polymer may be one of PMMA or Silastic.

Alternatively, each said telescopic member is formed as a frustro-conical unit, having the inside surfaces thereof screw-threaded and the distal parts of their outside surfaces threaded to engage with the inside surface of the externally-adjacent telescopic member, wherein to provide said locking means.

The intramedullary support strut may be adapted for anchoring a hip or shoulder hemi/total arthroplasty prosthesis.

Alternatively, the intramedullary support strut may be adapted for the intramedutlary fixation of diaphyseal fractures of long bones.

Alternatively, the intramedullary support strut may be adapted for the intramedullary fixation or anchoring of compression screw fixation system for isolated intertrochanteric and subtrochanteric fractures.

Alternatively, the intramedullary support strut may be adapted for the intramedullary fixation or anchoring of compression screw fixation system for combined intertrochanteric/subcapital femoral fractures with subtrochanteric fractures.

Alternatively, the intramedullary support strut may be adapted for the intramedullary fixation or anchoring of compression screw fixation system for subcapital or proximal humeral fractures not requiring arthroplasty.

DESCRIPTION OF FIGURES

FIG. 1(b) in extended configuration.

FIGS. 2(a) to 2(e) show alternative transverse cross-sectional profiles of the embodiment of FIG. 1(b), taken along A—A.

FIG. 3 shows in cross-sectional side view a portion of the embodiment of FIG. 1(b).

FIGS. 4(a) and 4(b) show in cross-sectional side view the embodiment of FIGS. 1(a) and 1(b), respectively, in retracted configuration inserted in a portal formed in the bone, and in the extended configuration, respectively, used as a support for fixation of a diaphyseal fracture.

FIGS. 5(a) and 5(b) show in cross-sectional side view the embodiment of FIGS. 1(a) and 1(b), respectively, comprising actuation means for extending the strut.

FIGS. 12(a) and 12(b) show in cross-sectional side view the embodiment of FIGS. 1(a) and 1(b), respectively, in retracted configuration inserted in a portal formed in the bone, and in the extended configuration, respectively, used as a support stem for a total arthroplasty.

FIGS. 13(a) and 13(b) show in cross-sectional side view the embodiment of FIGS. 1(a) and 1(b), respectively, in retracted configuration inserted in a portal formed in the bone, and in the extended configuration, respectively, used as a support for a screw fixation system.

DISCLOSURE OF INVENTION

The present invention is defined by the claims, the contents of which are to be read as included within the disclosure of the specification, and will now be described by way of example with reference to the accompanying Figures.

In the present specification, the term "distal" refers to a direction away from the trunk or body of the patient, while the term "proximal" refers to a direction towards the trunk or body of the patient.

Figure 1B:
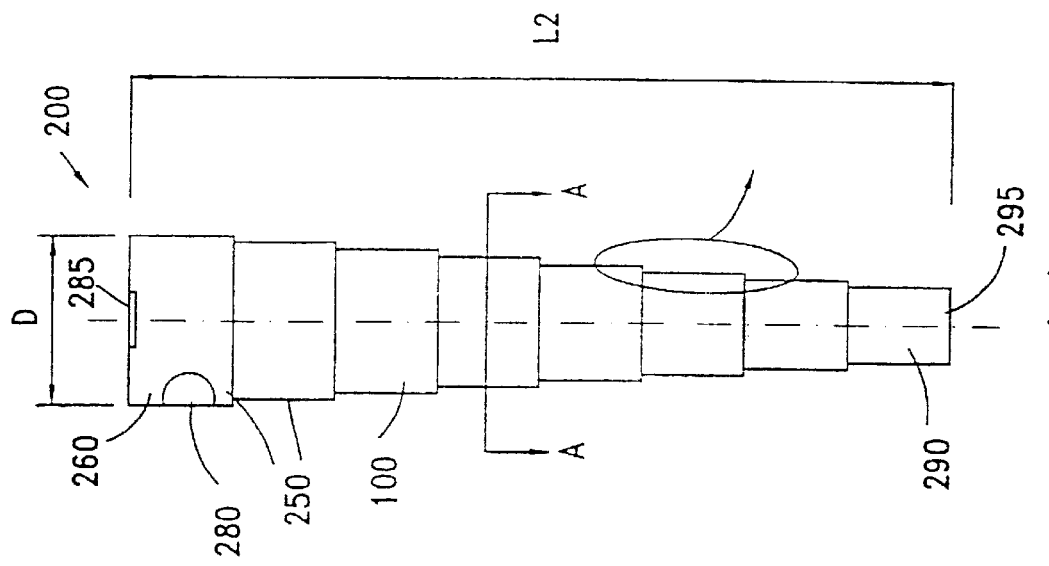
FIGS. 1(a) and 1(b) show in side view a preferred embodiment of the telescopic strut of the present invention FIG. 1(a) in retracted configuration.
Figure 1A:
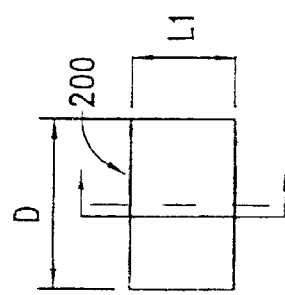

The present invention also relates to an intramedullary fixation particularly of sub-trochanteric and diaphyseal fractures of long bones, particularly for the femur or humerus. Referring to FIGS. 1(a) and 1(b), the support strut, generally designated (200) comprises at least two, and preferably a plurality of, telescopic elements or members (250) which are adapted for substantially linear movement relative to each other in a longitudinal direction, i.e., substantially parallel to the longitudinal axis (100) of the strut (200). In the preferred embodiment, said strut (200) comprises between 3 and 12, preferably between 6 and 10, and more preferably 8, said telescopic members (250). The strut (200) may thus be extended or expanded from a retracted configuration having a first length (L1) to an extended configuration having a second length (L2). In the preferred embodiment, the said telescopic members (250) are adapted for sliding longitudinal displacement relative to each other from said retracted to said extended configuration. Alternatively, said telescopic members (250) may be adapted for longitudinal displacement relative to each other from said retracted configuration to said extended configuration by each said telescopic member (250) having at least a portion of the inside surfaces thereof screw-threaded (not shown) and at least a portion of their outside surfaces complimentary threaded (not shown) to engage with the inside surface of the eternally-adjacent telescopic member (250).

As illustrated in FIGS. 4(a) and 4(b), the strut (200) is adapted for alignment with and expansion into a substantially longitudinal cavity (18) formed in the medullary canal of the long bone. With the strut (200) in the retracted configuration, the strut (200) is inserted into the long bone into a position aligned with the medullary cavity (18) via a substantially lateral portal (17) formed in the proximal part of the long bone. The strut (200) is further adapted for extending into said cavity (18) to the extended configuration to provide a support structure in said long bone. Thus, the telescopic strut (200) of the present invention comprises a compact profile in the retracted configuration, requiring minimally invasive surgical procedures for its insertion, in particular, via a portal (17) formed in the lateral part (19) of the bone.

Such a cavity (18) may be formed, for example, by first boring a portal (17) through the lateral cortex (19) of the particular long bone, e.g., the femur or humerus, typically opposite the neck thereof. The portal (17) may be substantially cylindrical, or indeed any other suitable cross-sectional shape. Advantageously, the portal (17) may comprise a cross-sectional profile substantially complementary to the transverse cross-sectional profile of the strut (200) in the retracted configuration, typically substantially rectangular. Then, a flexible reamer is introduced into the portal (17)

and guided in a manner known in the art such as to drill a longitudinal cavity (18) into the long bone, in particular the medullary canal thereof. Such procedures are well known, particularly in relation to intramedullary nailing, and is described, for example, in Campbell's Operative Orthopedics 7$^{th}$ Edition, pp 1697 to 1698.

Typically, and in the preferred configuration, the said telescopic members (250) comprise a substantially circular longitudinal cross-sectional profile, i.e., as viewed along the longitudinal axis (100) of the strut (200). In other configurations the telescopic members (250) may comprise triangular, rectangular, elliptical or polygonal, as illustrated in FIGS. 2(b) to 2(e), respectively, or indeed any other suitable longitudinal cross-sectional profile, also including a profile complementary to the inner transverse profile of the medullary canal.

The said strut (200) comprises in said retracted configuration a transverse profile, adapted for enabling said strut (200) to be inserted into the long bone via a suitable proximal portal (17) formed through the lateral cortex of the long bone, such as to enable said strut (200) to be aligned with and extended into said cavity (18) formed in the medullary canal. The term transverse profile of the strut (200) in said retracted configuration includes the size and/or shape of said strut (200), particularly in planes normal to the longitudinal axis (110) of the portal (17). Thus, both the shape and size of strut (200) are such as to enable the same to be inserted and navigated within portal (17) into alignment with the cavity (18). In its simplest form, then, the transverse profile of the strut (200) in the retracted configuration is substantially rectangular having maximum size at the centre of the strut (200). The diameter of a circle circumscribed on the largest such transverse profile is thus smaller, or at least not greater than, the diameter of the portal (17) (typically when the latter has a circular cross-section, for example), such as to enable the strut (200) to be inserted and navigated into alignment with the medullary canal and thus cavity (18) from a distal direction via a portal (17) in the long bone, such as the femur or humerus, for example. The portal (17) is specially bored into the long bone, e.g., the corresponding femur or humerus, at an angle α with the intended axis (100) of the cavity (18). In the femur, for example, the maximum diameter of the portal (17) is typically limited by the diameter of the neck of the femur, and/or the amount of bony tissue left in the greater and lesser trochanters such as to provide sufficient mechanical integrity of the upper part of the bone. Angle α is typically between about 150° and about 90°, but may also be greater than 150°, though rarely less than 90°.

Each telescopic member (250) comprises a distal end (252) and a proximal end (254). With the possible exception of the innermost telescopic member (290), the distal end (252) of each telescopic member (250) is adapted to retain the proximal end (254) of another telescopic member (250) distally adjacent thereto, and thus may comprise mutually engageable flanges (251) and shoulders (253), for example. The innermost telescopic member (290) need only have proximal end (254) retained by the distal element (252) of the adjacent telescopic member (250). The telescopic members (250) are preferably all substantially equal in axial length, and comprise a diminishing diameter from the outermost member (260) to the innermost member (290). Nonetheless, the strut (200) may be configured with telescopic members (250) having different thicknesses and lengths.

While the term "diameter" generally refers to a real diameter, it is also herein understood to refer to any suitable width dimension of the features including telescopic members (250), portal (17) or cavity (18) and so on, when these features are essentially non-cylindrical, including the maximum width, average width, equivalent diameter (i.e., the diameter of a circle having the same cross-sectional area as the feature), diameter of a circle circumscribed around the cross-sectional shape thereof, and so on.

The sidewalls (270) of the telescopic members are typically relatively thin, typically about 1 mm to about 2 mm to minimise the differences in transverse dimensions between the distally and the proximally disposed telescopic members (250).

Typically, the ratio between the said first length (L1) to said second length (L2) is about 1:10, or may be even higher, or may even lower including 1:2 or less, though in the preferred embodiment this ratio is about 1:8.

Also, the ratio between the said first length (L1) to the external diameter (D) of the strut (200) is typically between about 0.5 and about 2.0, and preferably about 1.25, though this ratio may be less than 0.5 or greater than 2.0.

The strut (200) may be made from any suitable biocompatible material, preferably a metal or metal alloy chosen from among:—stainless steel, titanium, titanium alloys, "supermetal" alloys including cobalt-chromium-molybdenum, and/or any suitable plastics or polymeric material, or indeed any other suitable material or combination of materials. When using a flowable polymer within the strut (200), as described hereinbelow, the strut (200) need only be sufficiently robust such as to expand into the cavity (18) without deforming or buckling, thereby providing a former for the flowable polymer, which when set and hardened in situ may provide the necessary load-bearing properties.

Optionally, the said strut (200) comprises fenestrations, typically a plurality thereof in each said telescopic member (250), and the strut (200) may be filled with bone and/or bone substitutes and/or biologically active agents (e.g. BMP's) to allow for bony ingrowth over time.

The said telescopic members (250) are thus slideable one over the other to enable the strut (200) to be expanded from its retracted configuration. In the retracted configuration, the telescopic members (250) are nested one within the other to form a compact unit. The most proximally disposed, ie., the outermost, of said telescopic members (250) constitutes a base member (260), and typically comprises an upper opening (285), and optionally or alternatively a lateral opening (280), for providing communication between the inside (255) of said telescopic members (250) and the outside of said base member (260).

The strut (200) may be expanded into its extended configuration in any one of a number of ways, and thus preferably comprises suitable actuation means for so doing. For example, and referring to FIGS. 5(a) and 5(b), said actuation means comprises a suitable liquid, such as a saline solution (typically 0.9% NaCl) for example, which is injected into the strut (200) via said opening (280), the cavity (18) having been formed previously. In such a case, the inside (255) of the telescopic strut (200) is lined with material suitable for rendering it hermetically sealed to air and/or liquid, and the innermost telescopic member (290) comprises an end cap (295). Preferably, though, the said strut (200) comprises an inflatable bag (256) capable of being inflated longitudinally via an opening (257) (in communication with opening (280)) preferably fitted with a non-return valve (282). As the liquid is injected into the bag via the opening (257), the bag (256) expands, preferentially extending in a longitudinal direction, pushing the telescopic members (250) in a distal direction and thereby expanding the strut (200).

Figure 6:
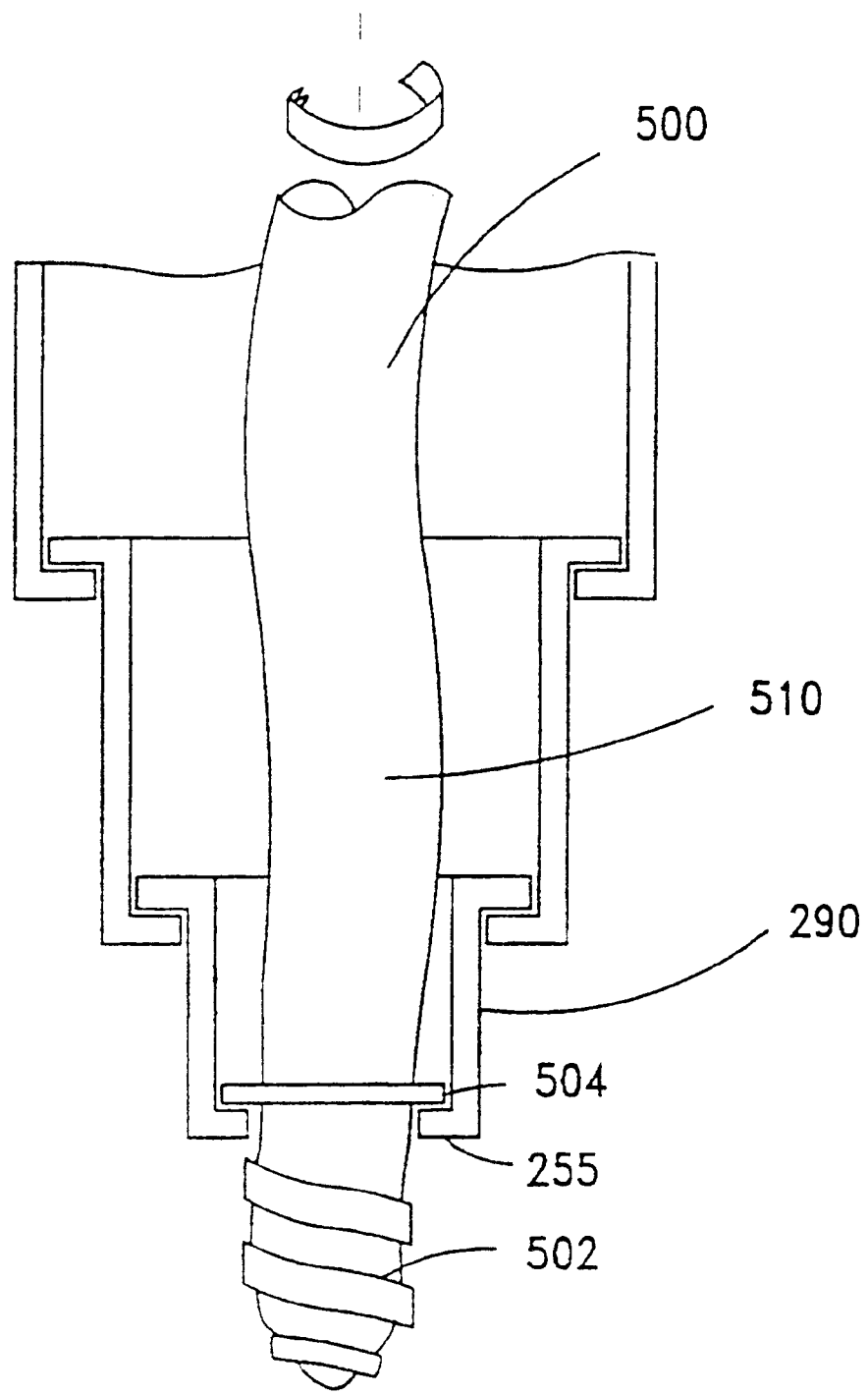
FIG. 6 shows in cross-sectional side view the embodiment of FIG. 1(b) comprising alternative actuation means and reaming means for extending the strut, and for reaming an additional distal cavity simultaneously with extending the distal part of the strut therein.

Alternatively, and as illustrated in FIG. 6, a flexible reamer reams out cavity (18) as before via portal (17), the cavity (18) having an internal diameter preferably slightly greater than that of the telescopic member adjacent to said base member (260). The same or another flexible reamer (500) having a special reamer head (502) at one end thereof and connected to a power tool outside the body via flexible driveshaft (510) is then used for extending the strut (200) to the open configuration. The reamer head (502) is rotatable by means of said power tool and comprises a shoulder (504) adapted for engagement or seating onto and rotating with respect to an annular flange (255) comprised in the innermost telescopic member (290). The reamer head (502) thus comprises a diameter no greater than that of the innermost telescopic member (290). The flexible reamer (500) may be inserted into the strut (200) via the upper aperture (285) (and therefore via an incision in the soft tissues and a correspondingly longitudinally aligned portal in the proximal part of the bone) such that the reamer head (502) is engaged into the orifice formed by said annular flange (255), with the reamer head (502) projecting distally therefrom. As the reamer (500) is advanced distally by the power tool it opens the telescopic strut (200). The longitudinal length of the cavity (18) is smaller than the fully extended length (L2) of the strut (200) by about the axial length of the innermost telescopic member (290). Thus, when the strut (200) reaches the distal end of the cavity (18), the reamer head (502) engages the bone and thus reams a further secondary cavity in the medullary canal approximately the diameter of the said innermost telescopic member (290), while simultaneously terminating the extension of the strut (200) to the full length (L2). Thus, the innermost telescopic member (290) is inserted into the secondary cavity of the medullary canal, providing a good anchoring point for the distal end of the strut (200).

Figure 7A:
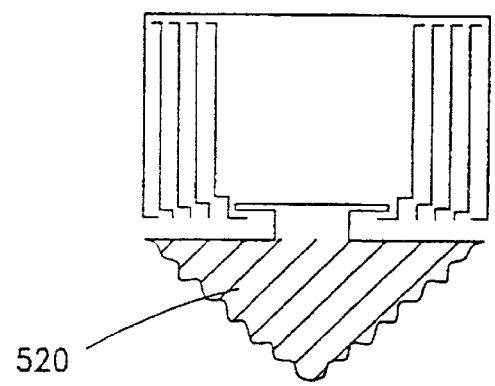
FIGS. 7(a) and 7(b) show in cross-sectional side view the embodiment of FIGS. 1(a) and 1(b), respectively, comprising alternative actuation means and reaming means for reaming the shaft and simultaneously extending the strut.
Figure 7B:
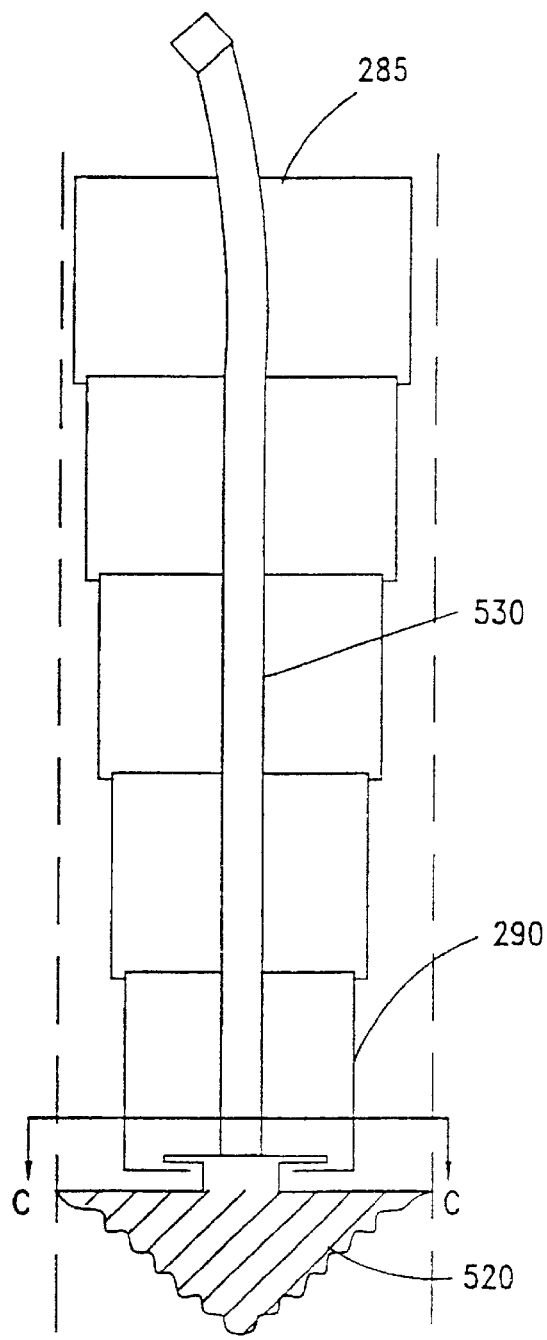
Figure 7C:
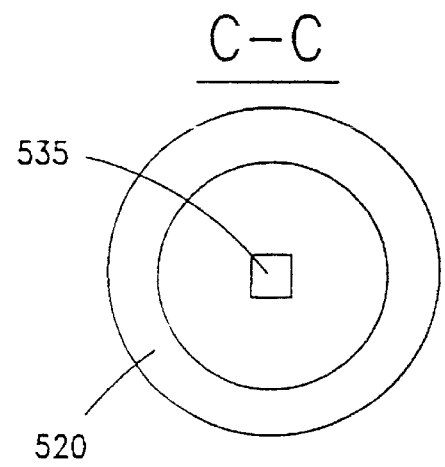
FIG. 7(c) shows the embodiment of FIG. 7(b) along C—C.

Alternatively, and as illustrated in FIGS. 7(a), 7(b) and 7(c), the innermost telescopic member (290) comprises a reamer head (520) rotatably mounted thereto, preferably permanently, and a flexible reamer driveshaft (530) is removably connected to the reamer head (520) at one thereof, and to a power tool at the other end thereof, to enable rotary motion to be transmitted to the reamer head (520). The reamer driveshaft (530) comprises a typically square transverse cross-section, and is releasably engageable with a complementary rectangular well (535) at the upper end of the reamer head (520). The reaming diameter of the reamer head (520) is at least equal to or greater than the diameter of the first telescopic member that extends into the shaft (18), i.e., the telescopic member (250) adjacent to the base member (260). This arrangement allows simultaneous reaming of the cavity (18) and opening of the strut (200), after which the flexible reamer driveshaft (530) can be disconnected from the reamer head (520). Typically, the strut (200) is positioned in the portal (17) (under fluoroscopy, for example) such that it is aligned with the centre of the medullary canal. A drill placement guide, such as for example that commonly used for anterior cruciate ligament reconstruction in the knee, as described in "Principles of Orthopedic Practice", ($2^{nd}$ Edition, by Dee, Hurst, Gruber & Kottmeier, pp 911–912) may be used for aligning the driveshaft (530) with the aperture (285), mutatis mutandis, and thus with the reamer head (520). Once activated, the reamer head (520) bores a shaft (18) coaxmal with said centre of the medullary canal, and simultaneously extends the strut (200) The reamer head (520) in such an arrangement remains in the bone, and provides means for possibly retracting the strut (200) by reattaching the flexible reamer shaft (530) thereto. The driveshaft (530) is inserted into the strut (200) via aperture (285) in the base member (260), (and therefore via an incision in the soft tissues and a correspondingly longitudinally aligned portal in the proximal part of the bone). When the reaming and extension operations are completed, the reamer driveshaft (530) is disengaged from the reamer head (520) and removed from the strut (200). Alternatively, the reamer head (520) comprises a diameter no greater than that of the innermost element (290), and is thus used only to ream a secondary cavity for this innermost element (290) after most of the strut (200) has been extended into a previously reamed cavity (18), in a similar manner to that described with reference to FIG. 6, mutatis mutandis, the major difference being that the driveshaft (530) is disengaged and removed, leaving the reamer head (520) in the bone with the strut (200). In such a case, the axial length of the innermost telescopic member (290) is preferably diminished in correlation to the axial length of the reamer head (520) such as to maintain the overall unextended length (L1) of the strut (200). Alternatively, the size of the portal (17) is increased to accommodate the larger dimensions of the strut (200) including the reamer head (520).

Figure 8:
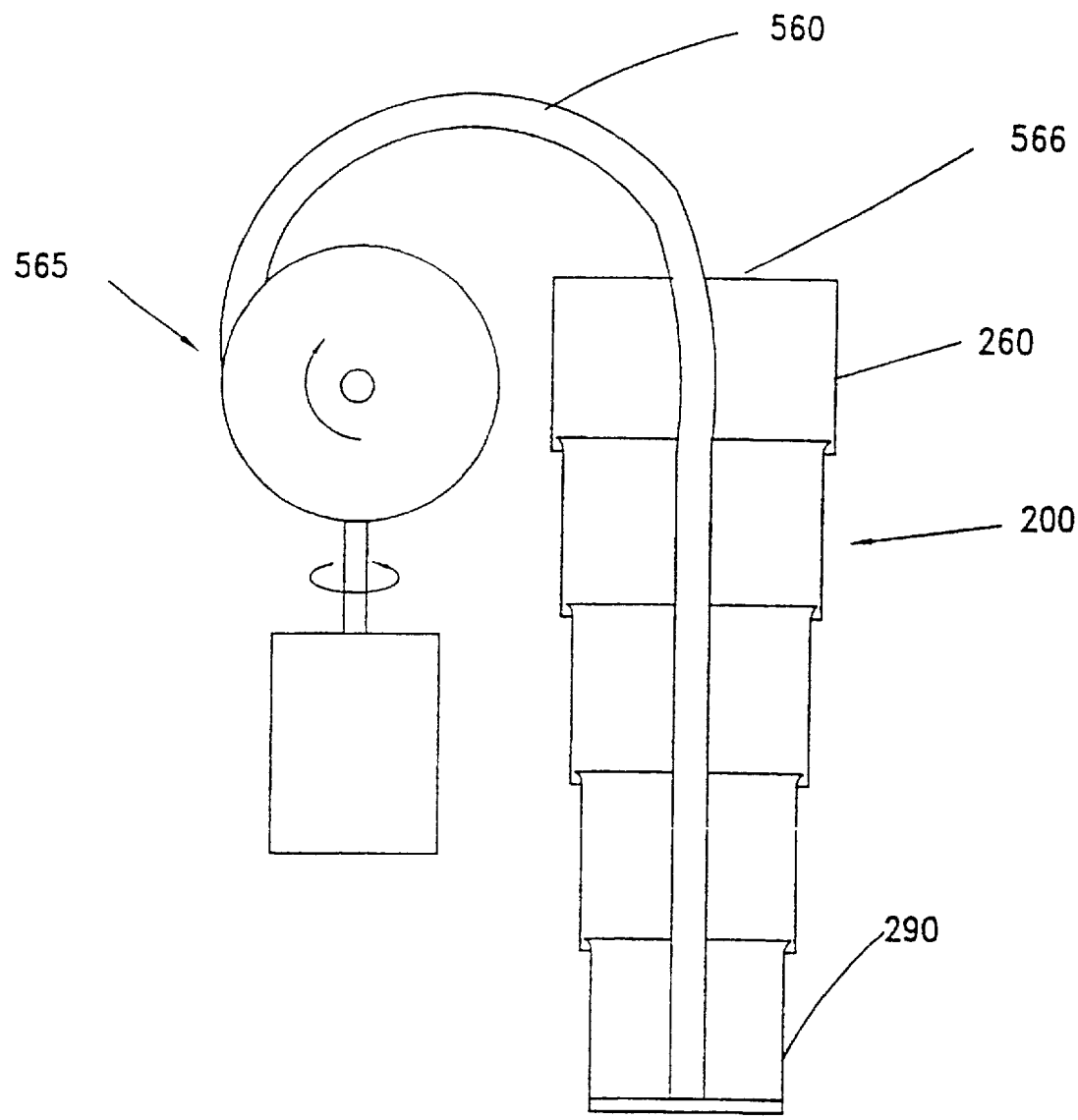
FIG. 8 shows in cross-sectional side view the embodiment of FIG. 1(b) comprising alternative actuation means for extending the strut.

Alternatively, and referring to FIG. 8, the said strut (200) may be extended by means of a flexible cable (560) attached at one end thereof to said innermost telescopic member (290) and at the other end thereof to a motorised winch arrangement (565) outside the body. The motorised winch arrangement (565) feeds the cable (560) into the strut (200) via a hole (566) in the upper end of the base member, forcing the strut (200) to extend. After the strut (200) is fully extended, the cable (560) may be cut as close as possible to the base member (260) and the portion of the cable (560) within the strut (200) retained therein.

Figures 9A, 9B:
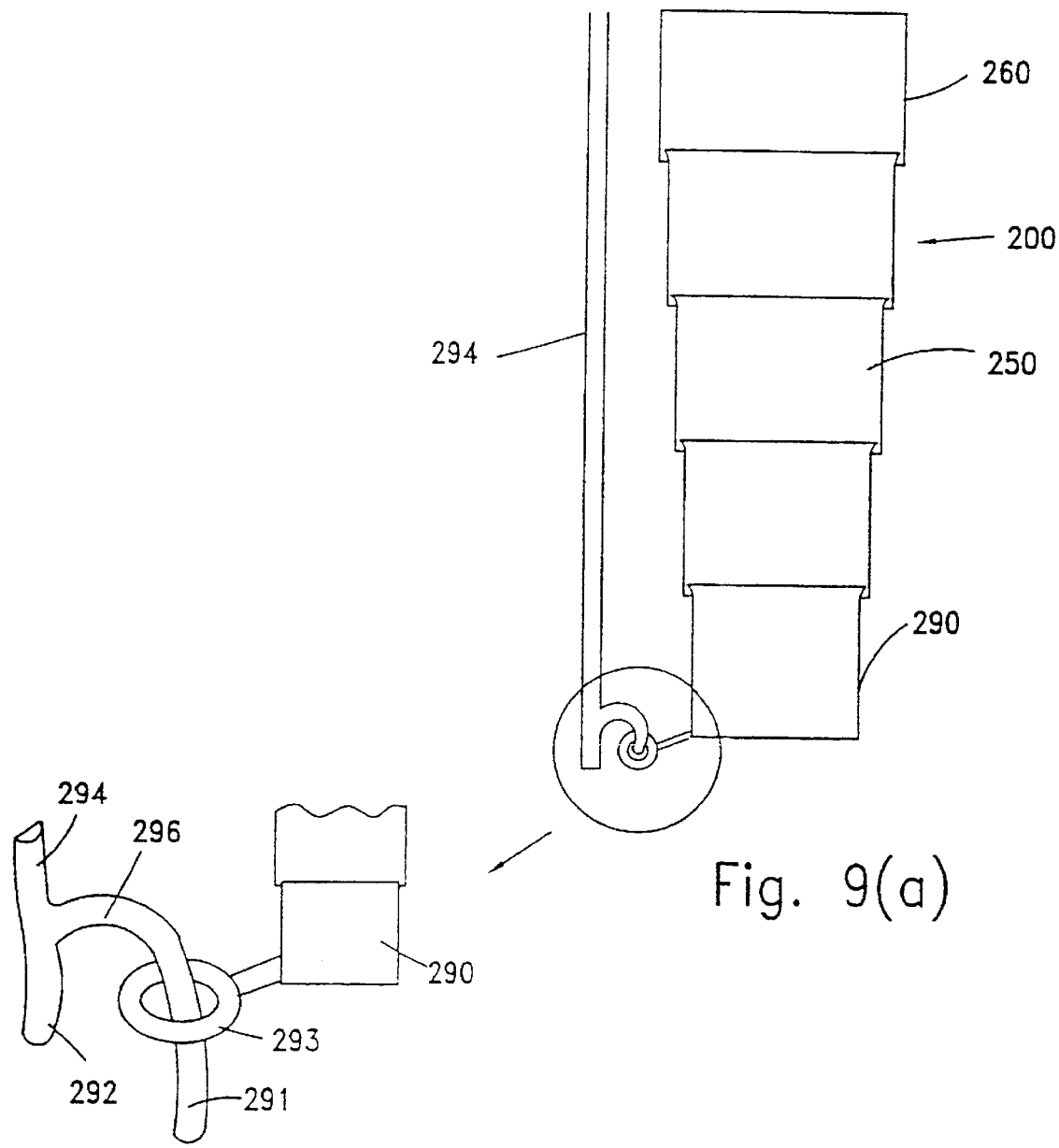
FIGS. 9(a) and 9(b) show in side view the embodiment of FIG. 1(b) comprising alternative actuation means for extending the strut.

Alternatively, and referring to FIGS. 9(a) and 9(b), the actuating means comprises a feeding wire arrangement comprising a wire (294) having a distal end in the form of a hook-like member (292). The hook-like member (292) has a probe portion (291) which is removably insertable through a ring member (293) attached to the distal end of said innermost telescopic member (290), such as to engage the U-shaped portion (296) of the hook-like member (292) with the ring member (293) in a distal direction. The probe portion (291) is preferably elongated so as to maintain the hook-like member (292) coupled to the ring member (293) even if the U-shaped portion is accidentally pulled a small displacement in a direction as to bring it out of engagement with the ring member (293). A wire feeder feeds said wire (294) distally with respect to said base member (260), enabling the hook-like member (292), which is engaged with ring member (293) to distally push the innermost telescopic member (290), and thereby the other telescopic members (250) enabling the strut (200) to extend distally. When fully extended, the wire (294) is simply pulled out, the hook-like member (292) automatically disengaging and decoupling from the ring member (293).

Preferably, the said telescopic members (250) are adapted for locking together when fully slid one relative to the other, and such locking may be accomplished in a number of ways using corresponding locking means.

For example, said locking means may be in the form of threaded surfaces comprised in said telescopic members (250), which enable each successive telescopic member (250) to rotate within and extend from an adjacent proximal telescopic member (250). Such threaded telescoping elements allow for at least nominal self-locking of the strut (200) once it is opened to the extended configuration. For example the telescopic members (250) may be formed as frustro-conical rather than cylindrical units, having the inside surfaces thereof screw-threaded and the distal parts of their outside surfaces threaded to engage with the inside surface of the externally-adjacent telescopic member (250). Each telescopic member (250) therefore has a larger proximal end and a smaller distal end. Thus, as each telescopic member (250) is unscrewed with respect to the externally-adjacent telescopic member (250) to extend in a longitudinal direction, the threaded engagement between the elements (250) gets tighter due to the sloping frustro-conical walls of the elements (250).

Alternatively, the locking means may comprise suitable interlocking stoppers (not shown) in the proximal and distal ends (254), (252), of each said telescopic member (250), to prevent the elements (250) from disengaging in their extended state and causing partial or total retraction of the strut (200).

Alternatively, the locking means may comprise a suitable flowable polymer that may be injected into the strut (200) such that sets and hardens in situ. In such an embodiment, the strut (200) preferably comprises a said cap (295), for example, to close the proximal end thereof, and the base member (260) comprises a suitable opening (280) through which the polymer may be injected. Examples of such polymers include PMMA, Silastic, or a two-component flowable polyurethane polymer manufactured by Advanced Bio-Surfaces of Minnetonka, (Minn., USA). Preferably, once set the polymer has flexural and structural characteristics similar to that of the bone.

Alternatively, the said locking means may comprise a liquid suitably maintained within the opened strut (200) under pressure. As illustrated in FIG. 5(b), the liquid, typically a 0.9% saline solution may be injected into the strut (200) via a one-way valve (282) at said opening (280), and the strut comprises an internal lining, though typically an inflatable bag (256), for preventing leakage and maintaining pressure of the liquid. The liquid may be injected after the strut (200) is opened, or may also be used as the actuation means for opening the strut (200), as hereinbefore described.

Figure 10:
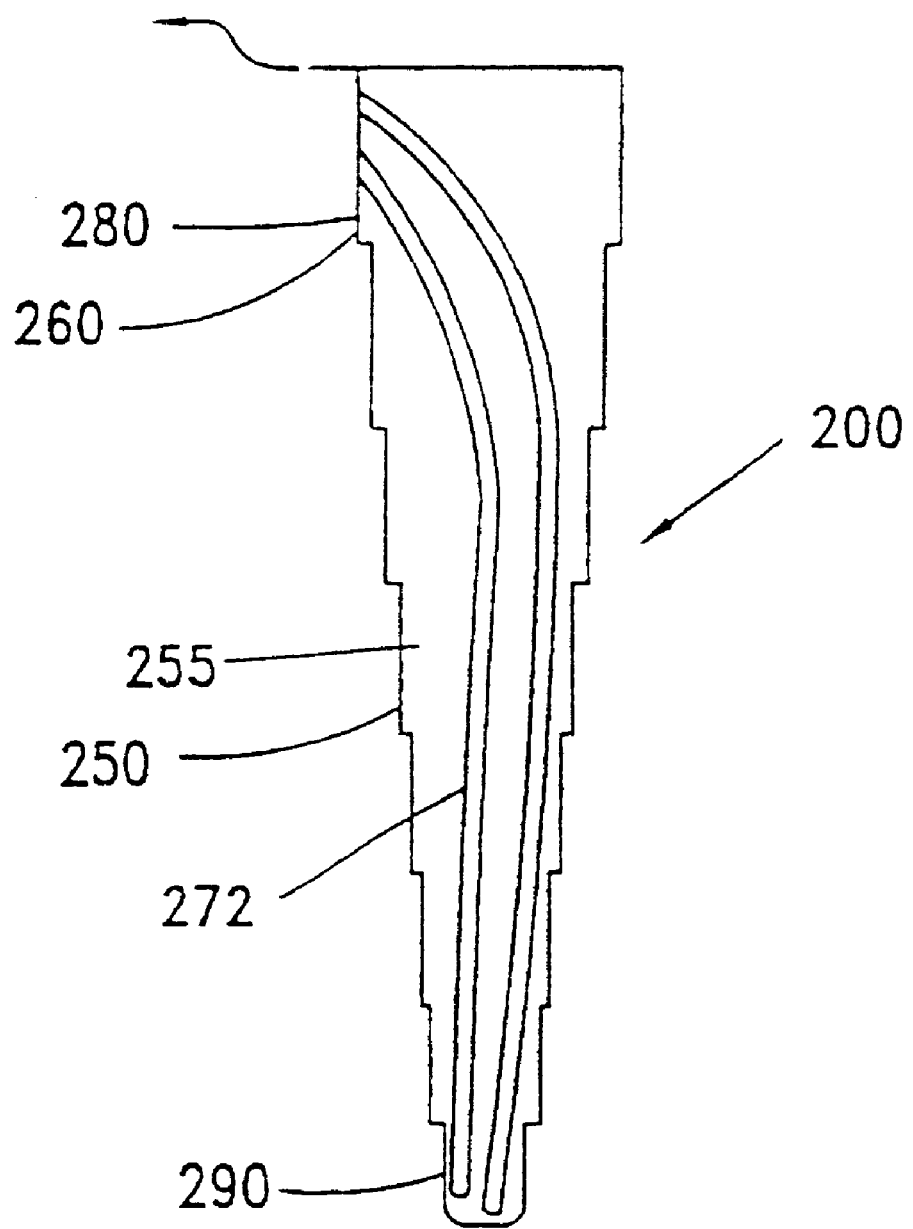
FIG. 10 shows in cross-sectional side view the embodiment of FIG. 1(b), comprising alternative locking means for locking the strut.

Alternatively, and referring to FIG. 10, said locking means may comprise an arrangement comprising one or more, and preferably two or three semi-rigid rods (272), for example, for maintaining the strut (200) in the open or extended configuration. Once the strut (200) is opened, the semi-rigid rods (272) are introduced into the strut (200) via opening (280) in the base member (260), by gently bending the rods (272). Once the rods (272) are fully inserted, the natural resilience thereof tend to maintain the rods as straight as possible, pushing against the two opposed longitudinal ends of the strut (200), thereby maintaining the strut (200) in the extended configuration. The rods (272) are kept from accidentally coming out the strut (200) by means of a suitable silicone cap, such as biocompatible silastic for example, that seals the lateral aperture (280) of the base member (260).

Alternatively, the locking means may comprise suitable adhesive, such as for example bone cement or biological glue, provided between said strut (200) and said cavity (18) when said strut (200) is in said extended configuration.

Figure 11:
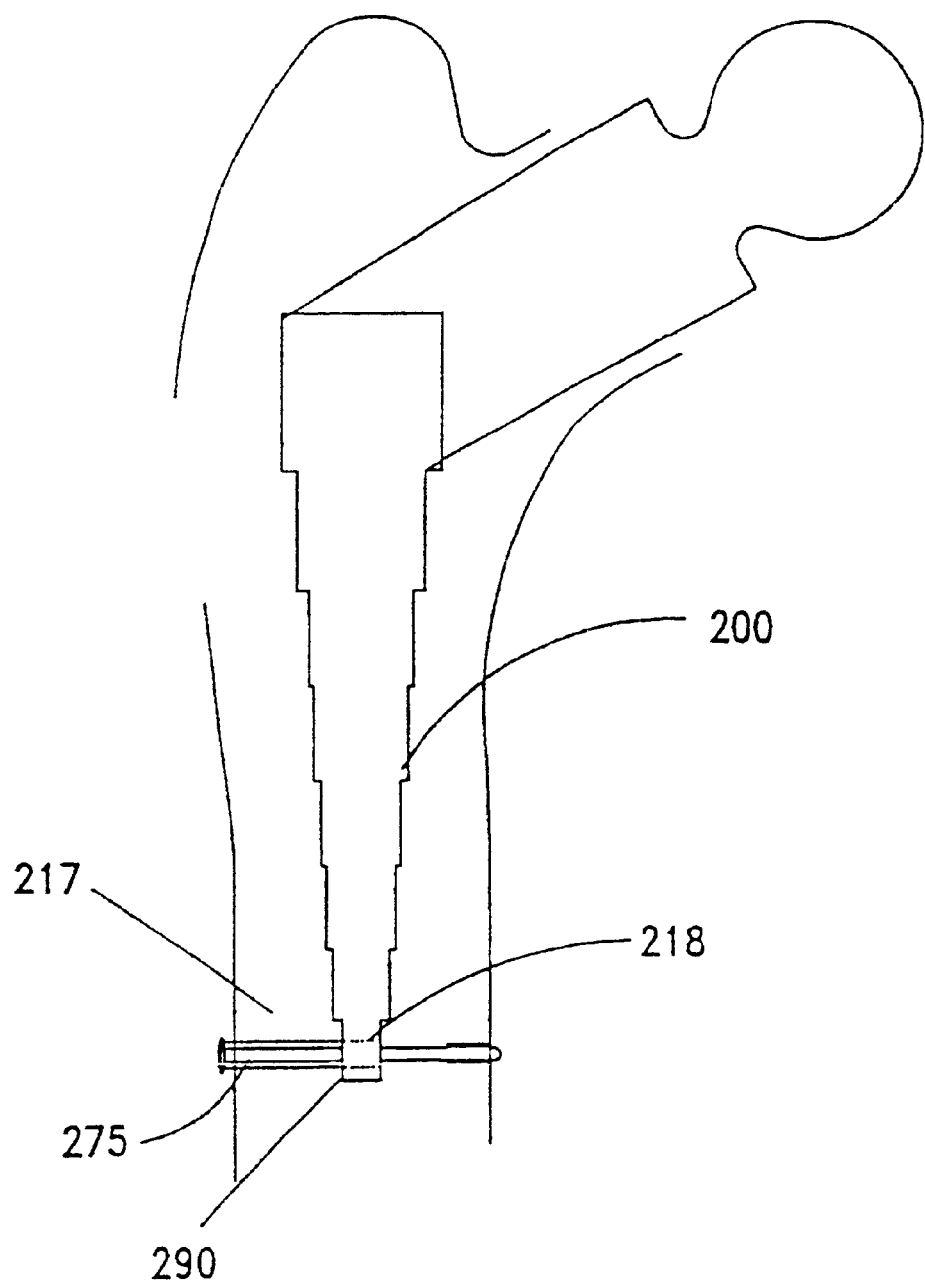
FIG. 11 shows in cross-sectional side view the embodiment of FIG. 1(b) comprising alternative locking means for locking the strut.

Alternatively, and referring to FIG. 11, said locking means comprises one or a plurality of locking screws or nails (275) for engaging the bone and strut (200) after it is opened.

Typically one or more locking screws or nails (275) may be inserted through corresponding lateral portals (217) formed in the distal part of the bone, e.g. the femur, the portals (217) being aligned with corresponding, preferably pre-prepared, holes (218) comprised in some of the telescopic members (250) and preferably including the innermost telescopic member (290), for example. Optionally, further nails (275) may engage the bone and strut (200) at various different positions.

The telescopic strut (200) of the present invention is highly versatile medullary fixation enabling its use in a variety of applications.

In some applications, the strut (200) acts as a medullary nail for holding together the distal and proximal parts of a fractured long bone, while in other applications, the strut (200) acts as an anchor for a head prosthesis for a femur or humerus, or for a compression screw used for neck fractures in these bones. In all cases, the strut (200) needs to transmit several types of loads, including torsion, bending and compression, at least from its proximal part to its distal part, and also to the bony tissue surrounding the strut within the cavity (18). Thus, the telescopic members (250) are typically, in the first instance, sufficiently robust at least to enable the strut (200) to expand into the cavity (18) without permanently buckling or deforming to any great extent. At this nominal condition, the strut (200) is preferably mechanically reinforced, in its expanded configuration, to render it mechanically compatible with the expected loads, and thus may be anchored to the bone surface in the medullary cavity (18) with suitable cement. Additionally or alternatively, a flowable polymer such as PMMA may be injected under pressure into the stem (200) via opening (280) so that it sets and hardens in situ.

Thus, in some applications, the said strut (200) may be used as an intramedullary fixation of diaphyseal fractures of long bones. As illustrated schematically in FIGS. 4(a) and 4(b), the strut (200) may be inserted while in its retracted configuration, into a portal (17) formed in the lateral cortex of the long bone, such as for example the femur or humerus, and aligned with cavity (18) formed in the medullary canal. The strut (200) is then extended, typically using actuation means as hereinbefore described, and optionally locked in place using locking means and optionally cemented in place, as hereinbefore described, providing a support for the long bone.

In some applications, and referring to FIGS. 12(a) and 12(b), the strut (200) may be used as the anchoring stem for hip and shoulder hemi/total arthroplasty prosthesis. Such applications involve the installation of a prosthesis (400) to replace the head of a femur or humerus, and the said base member (260) is joined to the distal end of the prosthesis (400). The prosthesis (400) may be a regular prosthesis, or alternatively an improved prosthesis as described in co-pending Israel Patent Application No. 133873, entitled "Improved Prosthesis", filed by the present applicant, the contents of which are included herein in their entirety. Such an improved ball prosthesis may be installed via a lateral portal such as portal (17) formed on the proximal part of the bone, and in such a case in particular, the said telescopic strut (200) provides a convenient way for anchoring the prosthesis (400), since no further surgical intervention is required for the strut (200) other than the formation of the medullary cavity (18). Thus, as much as possible of the long bone remains, preserving the mechanical integrity thereof. In such an application, the said outermost element (260) may be integral with, or removably or permanently attachable to, the cylindrical body of the prosthesis (400), and is thus automatically set at the required angle α with respect thereto. FIGS. 12(a) and 12(b) illustrate schematically such a prosthesis (400) incorporating a strut (200), with the strut (200) in the retracted and extended configurations, respectively.

In other applications, the said strut (200) may be used, for example, as an intramedullary fixation/anchoring mechanism of a compression screw/nail fixation system for isolated intertrochanteric and subtrochanteric fractures, or of a compression screw/nail fixation system for combined intertrochanteric/subcapital femoral fractures with subtrochanteric fractures, or of a compression screw fixation system for subcapital/proximal humeral fractures (which do not require arthroplasty), or the like. Such applications typically involve a compression nail or screw (300) for providing a compressive force between the head of the femur (or humerus) and the neck. Referring to FIGS. 13(a) and 13(b), illustrate schematically such a screw (300) incorporating a strut (200), with the strut (200) in the retracted and extended configurations, respectively. The said outermost member (260) may comprise a sleeve (320) having a suitable aperture for enabling the proximal end (330) of the screw (300) to be slidably received therein. A bolt (340) may be screwed into a complementary threaded shaft (345) of the said distal end (340) and against the sleeve (320) to maintain compression of the head of the bone with respect to the neck thereof. The portal (17) is sufficiently large so as to enable the strut (200) in the retracted configuration, including the sleeve (320) to be inserted therethrough to alignment with cavity (18) in the medullary canal. Of course, prior to actuating the screw arrangement, the strut (200) is extended and anchored in the shaft (18). Preferably, bonegraft removed from the neck area and/or provided from the formation of said portal (17) and/or cavity (18) may be packed around the mouth of the cavity (18) enabling the strut (200) to fit snugly in place.

The angle α formed between the filly extended strut (200) and the screw (300) or prosthesis (400), as well as the length (L2) of the fully extended strut (200), may be varied to account for anatomical variations between different patients and/or special surgical needs. The telescopic strut (200) adapted for use in the medullary canal of the humerus is essentially identical to one adapted for use in the femur, except for its smaller dimensions to allow it to fit in the narrower humeral canal.

While in the foregoing description describes in detail only a few specific embodiments of the invention, it will be understood by those skilled in the art that the invention is not limited thereto and that other variations in form and details may be possible without departing from the scope and spirit of the invention herein disclosed.

What is claimed is:

1. An intramedullary support strut for a long bone consisting of a plurality of elements, said plurality consisting of one terminal, a base member, and at least one extendable element; the first of said extendable elements being telescopically supported in said base member; the remaining extendable elements, if any, being telescopically connected to one another, whereby said support strut is extendable from a retracted configuration having a first longitudinal length to an extended configuration having a second longitudinal length; said support strut being adapted in said extended configuration for accommodation in a longitudinal cavity formed in the medullary canal of said long bone and for providing therein a mechanical support structure for said long bone and
being aligned with and extended into said longitudinal cavity.

2. An intramedullary support strut as claimed in claim 1, wherein said strut comprises a cap portion at the terminal end of the base member.

3. An intramedullary support strut as claimed in claim 1, wherein a first ratio of tKe diameter of said strut to said first length is between about 0.5 and about 2.0, and preferably about 1.25.

4. An intramedullary support strut as claimed in claim 1, wherein a second ratio of said second length to said first length is between about 2 and about 10, and preferably about 8.

5. An intramedullary support strut as claimed in claim 1, wherein said strut comprises between 3 and 10, and preferably 8 said telescopic members.

6. An intramedullary support strut as claimed in claim 1, wherein said telescopic members are adapted for sliding longitudinal displacement relative to each other from said retracted to said extended configuration.

7. An intramedullary support strut as claimed in claim 1, further comprising locking means for maintaining said strut in said extended configuration.

8. An intramedullary support strut as claimed in claim 7, wherein said locking means comprises suitable stops between adjacent said telescopic members adapted to prevent relative movement therebetween when said strut is in said extended configuration.

9. An intramedullary support strut as claimed in claim 7, wherein said locking means comprises an inflatable bag having an opening for receiving a suitable liquid, said bag adapted for maintaining said liquid at a suitable pressure.

10. An intramedullary support strut as claimed in claim 7, wherein said locking means comprises at least one semi-rigid bar insertable within said strut when said strut is in said extended configuration.

11. An intramedullary support strut as claimed in claim 7, wherein said locking means comprises a screw or nail for locking the said innermost telescopic member with respect to said long bone, when said strut is in said extended configuration.

12. An intramedullary support strut as claimed in claim 7, wherein said locking means comprises suitable adhesive, including bone cement or biological glue, provided between said strut and said cavity when said strut is in said extended configuration.

13. An intramedullary support strut as claimed in claim 7, wherein said locking means comprises a suitable flowable polymer injected into said strut when said strut is in said extended configuration, said flowable polymer being adapted for setting and hardening in situ.

14. An intramedullary support strut as claimed in claim 13, wherein said flowable polymer is one of PMMA or Silastic.

15. An intramedullary support strut as claimed in claim 7, wherein each said telescopic member is formed as a frustro-conical unit, having the inside surfaces thereof screw-threaded and the distal parts of their outside surfaces threaded to engage with the inside surface of the externally-adjacent telescopic member, wherein to provide said locking means.

16. An intramedullary support strut as claimed in claim 1, wherein said strut is adapted for anchoring a hip or shoulder hemi/total arthroplasty prosthesis.

17. An intramedullary support strut as claimed in claim 1, wherein said strut is adapted for the intramedullary fixation of diaphyseal fractures of long bones.

18. An intramedullary support strut as claimed in claim 1, wherein said strut is adapted for the intramedullary fixation or anchoring of compression screw fixation system for isolated intertrochanteric and subtrochanteric fractures.

19. An intramedullary support strut as claimed in claim 1, wherein said strut is adapted for the intramedullary fixation or anchoring of compression screw fixation system for combined intertrochanteric/subcapital femoral fractures with subtrochanteric fractures.

20. An intramedullary support strut as claimed in claim 1, wherein said strut is adapted for the intramedullary fixation or anchoring of compression screw fixation system for subcapital or proximal humeral fractures not requiring arthroplasty.

21. An intramedullary support strut for a long bone comprising at least two telescopic members adapted for longitudinal displacement relative to each other from a retracted configuration of said strut having a first longitudinal length to an extended configuration of said strut having a second longitudinal length, wherein said strut is adapted in said extended configuration for accommodation in a longitudinal cavity formed in the medullary canal of said long bone and for providing therein a mechanical support structure for said long bone, and is characterized in that said strut comprises in said retracted configuration a transverse profile adapted for enabling said strut to be inserted into said long bone via a suitable lateral portal formed through the lateral cortex of the long bone, such as to enable said strut to be aligned with and extended into said longitudinal cavity; and wherein each said telescopic member comprises a substantially circular longitudinal cross-sectional profile.

22. An intramedullary support strut for a long bone comprising at least two telescopic members adapted for longitudinal displacement relative to each other from a retracted configuration of said strut having a first longitudinal length to an extended configuration of said strut having a second longitudinal length, wherein said strut is adapted in said extended configuration for accommodation in a longitudinal cavity formed in the medulary canal of said long bone and for providing therein a mechanical support structure for said long bone, and is characterized in that said strut comprises in said retracted configuration a transverse profile adapted for enabling said strut to be inserted into said long bone via a suitable lateral portal formed through the lateral cortex of the long bone, such as to enable said strut to be aligned with and extended into said longitudinal cavity; and wherein each said telescopic member comprises a substantially elliptical longitudinal cross-sectional profile.

23. An intramedullary support strut for a long bone comprising at least two telescopic members adapted for longitudinal displacement relative to each other from a retracted configuration of said strut having a first longitudinal length to an extended configuration of said strut having a second longitudinal length, wherein said strut is adapted in said extended configuration for accommodation in a longitudinal cavity formed in the medullary canal of said long bone and for providing therein a mechanical support structure for said long bone, and is characterized in that said strut comprises in said retracted configuration a transverse profile adapted for enabling said strut to be inserted into said long bone via a suitable lateral portal formed through the lateral cortex of the long bone, such as to enable said strut to be aligned with and extended into said longitudinal cavity; and wherein each said telescopic member comprises a substantially triangular longitudinal cross-sectional profile.

24. An intramedullary support strut for a long bone comprising at least two telescopic members adapted for longitudinal displacement relative to each other from a retracted configuration of said strut having a first longitudinal length to an extended configuration of said strut having a second longitudinal length, wherein said strut is adapted in said extended configuration for accommodation in a longitudinal cavity formed in the medullary canal of said long bone and for providing therein a mechanical support structure for said long bone, and is characterized in that said strut comprises in said retracted configuration a transverse profile adapted for enabling said strut to be inserted into said long bone via a suitable lateral portal formed through the lateral cortex of the long bone, such as to enable said strut to be aligned with and extended into said longitudinal cavity; and wherein each said telescopic member comprises a substantially rectangular longitudinal cross-sectional profile.

25. An intramedullary support strut for a long bone comprising at least two telescopic members adapted for longitudinal displacement relative to each other from a retracted configuration of said strut having a first longitudinal length to an extended configuration of said strut having a second longitudinal length, wherein said strut is adapted in said extended configuration for accommodation in a longitudinal cavity formed in the medullary canal of said long bone and for providing therein a mechanical support structure for said long bone, and is characterized in that said strut comprises in said retracted configuration a transverse profile adapted for enabling said strut to be inserted into said long bone via a suitable lateral portal formed through the lateral cortex of the long bone, such as to enable said strut to be aligned with and extended into said longitudinal cavity; and wherein each said telescopic member comprises a substantially polygonal longitudinal cross-sectional profile.

26. An intramedullary support strut for a long bone comprising at least two telescopic members adapted for longitudinal displacement relative to each other from a retracted configuration of said strut having a first longitudinal length to an extended configuration of said strut having a second longitudinal length, wherein said strut is adapted in said extended configuration for accommodation in a longitudinal cavity formed in the medullary canal of said long bone and for providing therein a mechanical support structure for said long bone, and is characterized in that said strut comprises in said retracted configuration a transverse profile adapted for enabling said strut to be inserted into said long bone via a suitable lateral portal formed through the lateral cortex of the long bone, such as to enable said strut to be aligned with and extended into said longitudinal cavity; and further comprising actuating means for extending said strut from said retracted configuration to said extended configuration.

27. An intramedullary support strut as claimed in claim 26, wherein said actuating means comprises a liquid injected under pressure into said strut via a suitable opening therein.

28. An intramedullary support strut as claimed in claim 27, further comprising an inflatable bag in said strut and in communication with said opening for receiving said liquid and for preventing leakage of liquid therefrom.

29. An intramedullary support strut as claimed in claim 26, wherein said actuating means comprises a feeding wire arrangement comprising a wire having a distal end attached to the distal end of said innermost telescopic member, and a wire feeder for feeding said wire distally with respect to said base member.

30. An intramedullary support strut as claimed in claim 29, wherein said feeding wire is disposed external to said strut.

31. An intramedullary support strut as claimed in claim 29, wherein said feeding wire is disposed internally in said strut, and wherein said wire feeder comprises a spool for feeding said wire to said strut, said spool being operatively connected to a motor means.

32. An intramedullary support strut as claimed in claim 26, wherein said actuating means comprises a suitable reamer having a suitable reamer head at one end thereof rotatably mounted with respect to an innermost telescopic member, wherein rotation of said reamer head and advancement thereof in a distal direction by suitable rotation means automatically opens the said strut.

33. An intramedullary support strut as claimed in claim 32, wherein said rotation means comprises a suitable power tool.

34. An intramedullary support strut as claimed in claim 33, wherein said reamer comprises a flexible reamer driveshaft removably connected to the said reamer head at one thereof, and to said power tool at the other end thereof.

35. An intramedullary support strut as claimed in claim 34, wherein a reaming diameter of said reamer head is at least equal to or greater than the diameter of said base member.

36. An intramedullary support strut as claimed in claim 26, wherein said actuating means comprises a suitable reamer having a suitable reamer head at one end thereof releasably rotatably engageable with respect to an innermost telescopic member, wherein rotation of said reamer head and advancement thereof in a distal direction by suitable rotation means automatically opens the said strut.

37. An intramedullary support strut as claimed in claim 36, wherein a reaming diameter of said reamer head is smaller than the diameter of said innermost telescopic member.

38. A method for the fixation of fractures of long bones, comprising the steps of:
   a) providing a support strut comprising at least two telescopic members adapted for longitudinal displacement relative to each other, from a retracted configuration of said strut to an extended configuration of said strut, wherein said strut is adapted in said extended configuration for accommodation in a longitudinal cavity formed in the medullary canal of said long bone and for providing therein a mechanical support structure for said long bone;
   b) boring a portal through the lateral cortex of said long bone, such that a cross-sectional profile of said portal is substantially complementary to a transverse profile of said strut, in said retracted configuration;
   c) forming said cavity by guiding a reamer into the medullary canal of said long bone;
   d) introducing said strut in said retracted configuration into said portal; and
   e) expanding said strut to said extended configuration, until distal and proximal parts of a fractured long bone are held together.

39. The method according to claim 38, wherein said support strut is locked in said extended configuration.

40. A method for anchoring a hip or shoulder hemi/total arthroplasty prosthesis, comprising the steps of:
   a) providing a support strut comprising at least two telescopic members adapted for longitudinal displacement relative to each other, from a retracted configuration of said strut to an extended configuration of said strut, wherein said strut is adapted in said extended configuration for accommodation in a longitudinal cavity formed in the medullary canal of a long bone and for providing therein a mechanical support structure for said long bone;
   b) boring a lateral portal on the proximal part of said long bone;
   c) forming said cavity by guiding a reamer into the medullary canal of said long bone;
   d) joining the outermost telescopic member to a body of a prosthesis;
   e) introducing said strut in said retracted configuration into said portal; and
   f) expanding said strut to said extended configuration, until said prosthesis is anchored.

41. A method for applying a compressive force between the head and neck of a long bone, in order to fixate a fracture, comprising the steps of:
   a) providing a support strut comprising at least two telescopic members and a sleeve formed in the outermost member, said telescopic members adapted for longitudinal displacement relative to each other, from a retracted configuration of said strut to an extended configuration of said strut, wherein said strut is adapted in said extended configuration for accommodation in a longitudinal cavity formed in the medullary canal of said long bone and for providing therein a mechanical support structure for said long bone;
   b) boring a portal through the lateral cortex of said long bone;
   c) forming said cavity by guiding a reamer into the medullary canal of said long bone;
   d) introducing said strut in said retracted configuration into said portal;
   e) expanding said strut to said extended configuration, until said strut is anchored in said cavity;
   f) introducing a screw or nail of a fracture fixation system into a proximal end of said sleeve, said screw or nail extending into the head and neck of said long bone; and
   g) engaging a bolt into a complementary threaded shaft of the distal end of said sleeve, whereby a compressive force is applied to said screw or nail.

42. The method according to claim 41, wherein the fracture to be fixated is selected from the group consisting of isolated intertrochanteric and subtrochanteric fractures, combined intertrochanteric/subcapital femoral fractures with subtrochanteric fractures, subcapital/proximal humeral fractures, or the like.

* * * * *

UNITED STATES PATENT AND TRADEMARK OFFICE
CERTIFICATE OF CORRECTION

PATENT NO. : 6,755,862 B2 Page 1 of 1
DATED : June 29, 2004
INVENTOR(S) : Ory Keynan It is certified that error appears in the above-identified patent and that said Letters Patent is hereby corrected as shown below:

Column 14,
Line 5, change "tKe" to -- the --.

Signed and Sealed this

Nineteenth Day of October, 2004

JON W. DUDAS
*Director of the United States Patent and Trademark Office*